(12) United States Patent
Sharp et al.

(10) Patent No.: US 8,262,567 B2
(45) Date of Patent: Sep. 11, 2012

(54) TISSUE RETRACTOR, TISSUE RETRACTOR KIT AND METHOD OF USE THEREOF

(75) Inventors: Brad Sharp, Irvine, CA (US); Stephen Graham Bell, Rome (IT); Wayne Arthur Noda, Mission Viejo, CA (US); Laxmikant Khanolkar, Mumbai (IN); Meng Pheng Tan, Singapore (SG); Yin Chiang Boey, Singapore (SG); Jan Ma, Singapore (SG); Erwin Merijn Woterson, Singapore (SG)

(73) Assignees: Insightra Medical, Inc., Irvine, CA (US); Nanyang Technological University, Singapore (SG)

( * ) Notice: Subject to any disclaimer, the term of this patent is extended or adjusted under 35 U.S.C. 154(b) by 521 days.

(21) Appl. No.: 11/677,975

(22) Filed: Feb. 22, 2007

(65) Prior Publication Data

US 2007/0232864 A1 Oct. 4, 2007

Related U.S. Application Data

(60) Provisional application No. 60/744,017, filed on Mar. 31, 2006.

(51) Int. Cl.
*A61B 1/32* (2006.01)
(52) U.S. Cl. ...................................... 600/206
(58) Field of Classification Search ........... 600/201–246
See application file for complete search history.

(56) References Cited

U.S. PATENT DOCUMENTS

| 2,493,598 A | * | 1/1950 | Rozek ........................... 600/229 |
| 2,717,437 A | | 9/1955 | de Mestral |
| 4,412,532 A | * | 11/1983 | Anthony ....................... 600/206 |
| 4,430,991 A | | 2/1984 | Darnell |
| 4,621,619 A | | 11/1986 | Sharpe |
| 5,785,649 A | | 7/1998 | Fowler, Jr. |

(Continued)

FOREIGN PATENT DOCUMENTS

EP 1011467 8/2008

(Continued)

OTHER PUBLICATIONS

Written Opinion of the International Preliminary Examining Authority (PCT Rule 66) in PCT/US2007/062609, Date of Mailing Feb. 21, 2008.

(Continued)

*Primary Examiner* — Eduardo C Robert
*Assistant Examiner* — Steven Cotroneo
(74) *Attorney, Agent, or Firm* — John L. Rogitz; John M. Rogitz

(57) ABSTRACT

A tissue retractor for retracting tissue opened by an incision, the tissue retractor including a base support unit having a topside and an underside. The topside has at least one securing mechanism and the underside is conformable and removably attachable to a surface proximate to the incision. The tissue retractor has a tissue hook having a tissue engagement portion and a mounting portion, the tissue engagement portion capable of engaging at least the periphery of the incision. The tissue retractor has a retractable member substantially inelastic in its central longitudinal axis and bendable in any axes deviating from the central longitudinal axis. The retractable member receives the mounting portion of the tissue hook, the retractable member being removably attachable to said securing mechanism on the topside of the base support unit, and being retractable away from the incision, such that the tissue engagement portion retracts tissue engaged thereto.

25 Claims, 14 Drawing Sheets

U.S. PATENT DOCUMENTS

| | | | |
|---|---|---|---|
| 5,899,853 A | 5/1999 | Fowler, Jr. | |
| 5,964,698 A * | 10/1999 | Fowler | 600/217 |
| 6,764,444 B2 * | 7/2004 | Wu et al. | 600/206 |
| 6,824,511 B1 | 11/2004 | Bell | |
| 6,932,765 B2 * | 8/2005 | Berg | 600/231 |
| 7,022,069 B1 | 4/2006 | Masson | |
| 7,309,312 B2 * | 12/2007 | Bjork et al. | 600/231 |
| 2003/0092969 A1 * | 5/2003 | O'Malley et al. | 600/216 |
| 2004/0133078 A1 * | 7/2004 | Edoga et al. | 600/227 |
| 2004/0158261 A1 * | 8/2004 | Vu | 606/114 |
| 2004/0186356 A1 * | 9/2004 | O'Malley et al. | 600/231 |
| 2004/0230099 A1 * | 11/2004 | Taylor et al. | 600/204 |
| 2004/0254427 A1 | 12/2004 | Fowler, Jr. | |
| 2005/0171404 A1 * | 8/2005 | Mische | 600/231 |
| 2005/0215865 A1 * | 9/2005 | LeVahn et al. | 600/231 |
| 2006/0064125 A1 | 3/2006 | Henderson | |
| 2006/0074278 A1 | 4/2006 | Petit | |
| 2006/0206009 A1 * | 9/2006 | Von Wald et al. | 600/231 |
| 2006/0270909 A1 * | 11/2006 | Davis et al. | 600/210 |
| 2007/0156023 A1 * | 7/2007 | Frasier et al. | 600/206 |
| 2007/0238933 A1 * | 10/2007 | Alinsod et al. | 600/231 |
| 2008/0234551 A1 * | 9/2008 | Lin et al. | 600/235 |

FOREIGN PATENT DOCUMENTS

| | | |
|---|---|---|
| GB | 2 223 410 | 4/1990 |
| WO | 9629013 A1 | 9/1996 |
| WO | 0025693 A1 | 5/2000 |
| WO | 03013368 | 2/2003 |
| WO | 2005070283 A1 | 8/2005 |

OTHER PUBLICATIONS

Office Action issued by the Chinese Patent Office for the corresponding Chinese patent application No. 2007800123758.

English Translation of Office Action issued by the Chinese Patent Office for the corresponding Chinese patent application No. 2007800123758.

* cited by examiner (i) (ii) (iii)

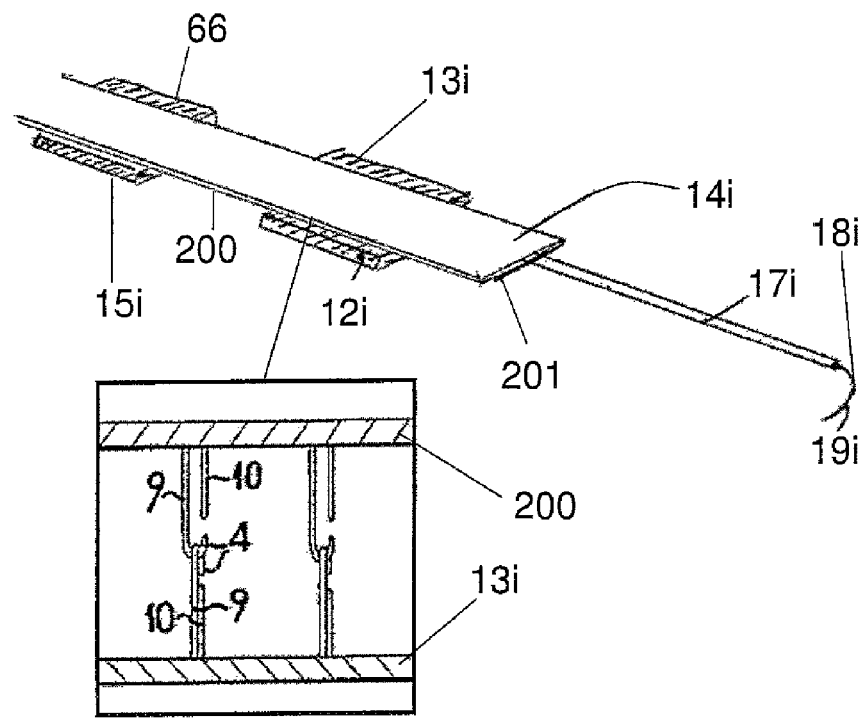
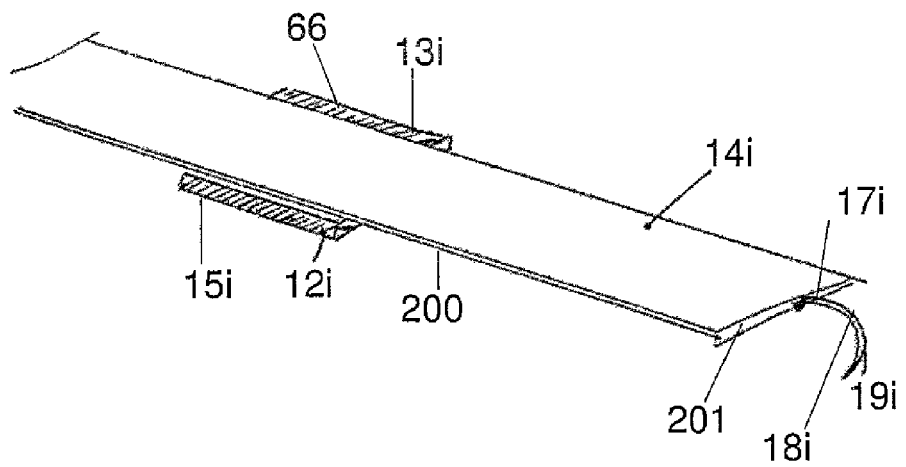

TISSUE RETRACTOR, TISSUE RETRACTOR KIT AND METHOD OF USE THEREOF

CROSS REFERENCE TO RELATED APPLICATION DATA

The present application is related to and claims the benefit of U.S. provisional application 60/744,017, titled "Tissue Retractor System", filed on Mar. 31, 2006, the entire contents of which is incorporated herein by reference for all purposes.

TECHNICAL FIELD

The present invention relates to the field of tissue retractors, and more specifically, to a tissue retractor and a tissue retractor kit for retracting tissue opened by an incision and to a method of use thereof.

BACKGROUND

During the course of a surgical procedure, a surgeon opens tissue of a patient by first making at least one incision typically using a scalpel. After the incision is made in the tissue, refractors are then used to retract the periphery of the incision in order to open the incision further. Once retracted, the open incision allows the surgeon to access other tissues or organs within the body, for example. Apart from just providing access, the tissue retractors serve to stabilize and present said retracted tissue in an orientation that is optimal for the surgeon to operate on.

During the retraction of incised tissue, care must be taken to avoid inflicting new, or as the case may be, additional trauma such as bruising, for example. Bruising may also be caused by viscoelastic forces inherently present in the contracting muscles or tissues of the patient, as said contracting muscles or tissues work against the forces exerted thereon by the retractor. Accordingly, it is important to exercise care in the application of external forces typically requiring additional operating personnel during surgical procedures in order to minimize the possibility of causing any bruising or even tearing of the tissue during surgery.

In order to accommodate the aforesaid requirements of a tissue retractor (or surgical retractor), elastic surgical retractor systems have been used. Such elastic retractor systems typically include an elongated elastic member that is typically a length of hollow tubing. The elastic tube has its one end connected to a hooking mechanism adapted to engage with the incised tissue, in particular, along the periphery of the incision.

However, there is still a need for a tissue retractor that is easy to use, compact of a low-profile, portable and is yet cost-effective to manufacture, as recognized by the present invention.

SUMMARY

A first aspect of the present invention relates to a tissue retractor including a base support unit, said base support unit having a topside and an underside. The topside includes at least one securing mechanism and the underside is adapted to be conformable and to be removably attachable to a surface proximate to an incision. The tissue retractor also includes at least one tissue hook having a tissue engagement portion and a mounting portion. The tissue engagement portion is capable of engaging at least a portion of the periphery of tissue opened by the incision. The tissue retractor also includes a retractable member substantially inelastic in its central longitudinal axis and flexible in at least one axis deviating from said central longitudinal axis. The retractable member is adapted to receive the mounting portion of the at least one tissue hook, wherein said retractable member is adapted to be removably attachable to said securing mechanism on the topside of the base support unit. The retractable member is retractable away from the incision, such that the tissue engagement portion retracts tissue to which it is engaged.

A second aspect of the present invention relates to a base support unit of a tissue retractor. The base support unit includes a topside; and an underside being adapted to be conformable and to be removably attachable to a surface proximate to tissue opened by an incision. The base support unit is adapted to form an opening, which extends from the topside through to the underside, and said opening surrounds the incision thereby providing access to the opened tissue surface beneath the base support unit.

A third aspect of the present invention relates to a tissue retractor kit. The kit includes at least one base support unit, said base support unit comprising a topside; and an underside being adapted to be conformable and to be removably attachable to a surface proximate to tissue opened by an incision. The base support unit is adapted to form an opening, which extends from the topside through to the underside, and said opening surrounds the incision thereby providing access to the opened tissue surface beneath the base support unit. The kit also includes at least one securing mechanism removably attachable to the topside and proximate to the opening; and a tissue hook and at least one retractable member. Each tissue hook comprises a tissue engagement portion and a mounting portion, said tissue engagement portion being capable of engaging at least the periphery of the tissue opened by the incision. Each retractable member is at least substantially inelastic in its central longitudinal axis and flexible in any axis deviating from said central longitudinal axis. The retractable member is adapted to receive the tissue hook at its mounting portion, wherein said retractable member is adapted to be removably attachable to said securing mechanism, and wherein said retractable member is retractable away from the incision, such that the tissue engagement portion retracts tissue to which it is engaged. In this respect, the invention also provides a two-part kit wherein the first part includes at least one base support unit, at least one securing mechanism removably attachable to the base support unit and at least one retractable member; and the second part includes at least one tissue hook adapted to attach to the retracting member.

A fourth aspect of the present invention relates to a method that retracts tissue opened by an incision with a tissue retractor including a base support unit, said base support unit having a topside and an underside. The topside includes at least one securing mechanism and the underside is adapted to be conformable and to be removably attachable to a surface proximate to an incision. The tissue retractor also includes at least one tissue hook having a tissue engagement portion and a mounting portion. The tissue engagement portion is capable of engaging at least a portion of the periphery of tissue opened by the incision. The tissue retractor also includes a retractable member substantially inelastic in its central longitudinal axis and flexible in at least one axis deviating from said central longitudinal axis. The retractable member is adapted to receive the at least one tissue hook at its mounting portion, wherein said retractable member is adapted to be removably attachable to said securing mechanism on the topside of the base support unit. The retractable member is retractable away from the incision, such that the tissue engagement portion retracts tissue to which it is engaged. The method includes attaching the base support unit on the surface proximate to the incision; connecting the retractable member to the mounting portion of the tissue hook; engaging the tissue hook with at least the periphery of the incision; retracting the retractable member away from the incision, such that the tissue engagement portion of the tissue hook retracts tissue it is engaged with to a predetermined distance; and securing the retracted retractable member to the securing mechanism on the topside of the base support unit.

A fifth aspect of the present invention relates to a method that retracts tissue opened by an incision including attaching a base support unit on the surface proximate to the incision, wherein the base support unit comprises a topside; and an underside being adapted to be conformable and to be removably attachable to a surface proximate to the incision. The base support unit is adapted to form an opening, which extends from the topside through to the underside, and said opening surrounds tissue opened by the incision thereby providing access to the opened tissue surface beneath the base support unit. The base support unit is positioned such that the opening surrounds the incision and provides access to the tissue surface beneath the base support unit.

BRIEF DESCRIPTION OF THE DRAWINGS

The various aspects of the present invention will be further described with reference to the following figures in which:

FIGS. 2A-2D illustrate an exemplary embodiment of a tissue retractor including a hook and loop fastener strip;

DETAILED DESCRIPTION AND EXEMPLARY EMBODIMENTS

FIGS. 1A-1H illustrate exemplary embodiments of tissue retractors that disclose the general principles of a tissue retractor according to the present invention. The present invention will be explained in the following with reference to these figures.

Figure 1A:
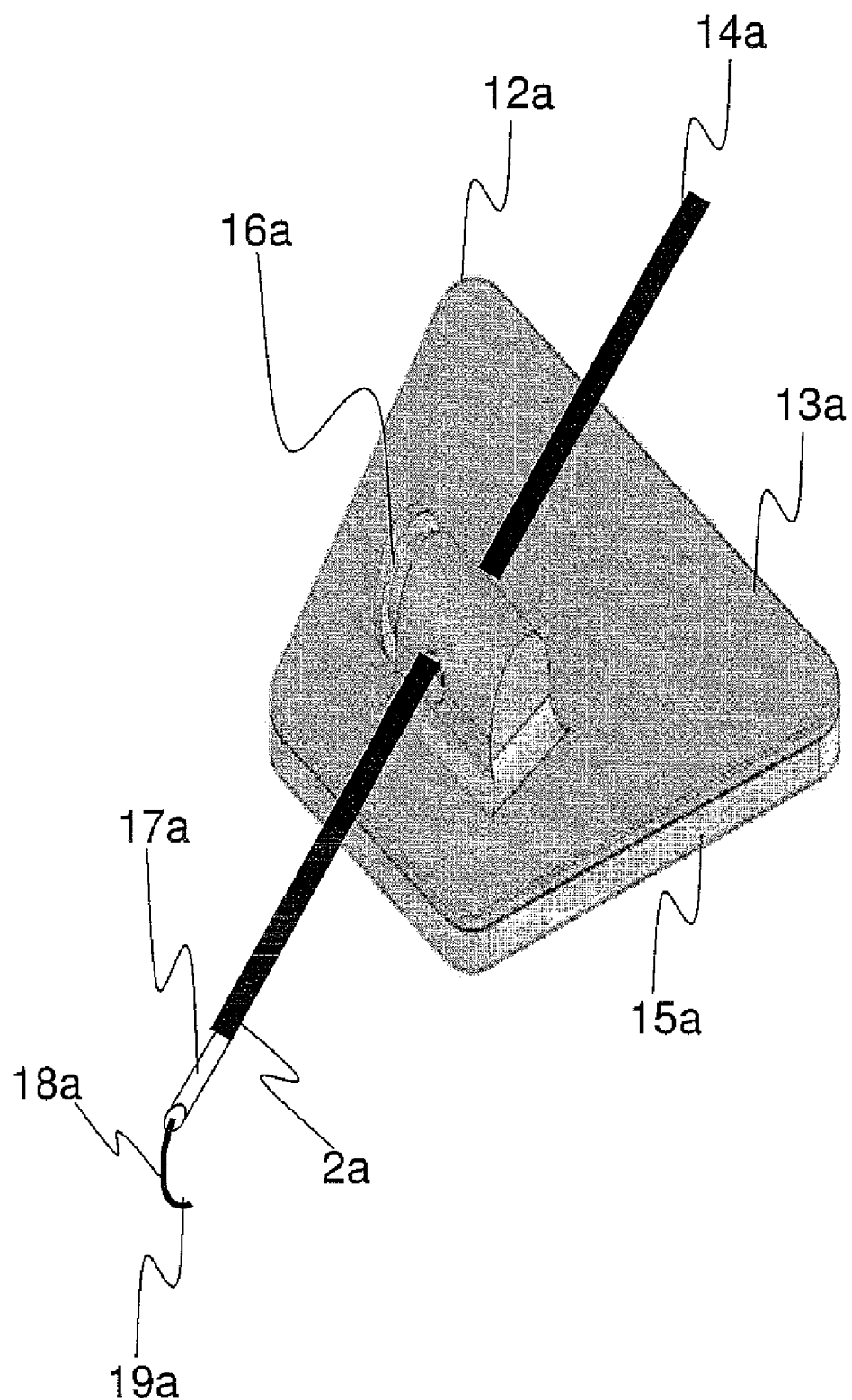
FIGS. 1A-1H illustrate various exemplary embodiments of a tissue retractor according to the present invention.

Referring first to the tissue retractor of FIG. 1A, the tissue retractor includes a base support unit 12a having a topside 13a and an underside 15a. The topside 13a includes at least one securing mechanism 16a and the underside 15a is adapted to be conformable, and to be removably attachable, to a surface proximate to an incision (not shown). The tissue retractor of FIG. 1A also includes at least one tissue hook 18a having a mounting portion 17a and a tissue engagement portion 19a. The tissue engagement portion 19a is capable of engaging at least a portion of the periphery of tissue opened by the incision. The tissue retractor of FIG. 1A also includes a retractable member 14a. The retractable member 14a is substantially inelastic in its central longitudinal axis (i.e. it is not stretchable) and is flexible in at least one axis that deviates from said central longitudinal axis. The retractable member 14a includes an end 2a that is adapted to receive the mounting portion 17a of the at least one tissue hook 18a.

In this exemplary embodiment of FIG. 1A, the mounting portion 17a of the tissue hook 18a is essentially a tube that is hollow and diametrically elastic. In this embodiment, the end 2a of the retractable member 14a is a rod-like structure that is diametrically larger than the tube 17a. As such, when the end 2a is assembled with the tube 17a, via an insertion, a tight fit, form fit or snap fit may take place. Alternatively, the tube 17a may be bonded to the retractable member 14a using adhesives or thermal bonding, for example.

As also illustrated in the exemplary embodiment of FIG. 1A, the retractable member 14a is also adapted to be removably attachable to said securing mechanism 16a on the topside 13a of the base support unit 12a. In this embodiment, the securing mechanism 16a is a releasable clamp, which may be spring-loaded, for example, through which the retractable member 14a is threaded through. When the retractable member 14a is retracted away from the incision (and towards the base unit 12a, which is stationary), the tissue engagement portion 19a retracts tissue to which it is engaged, thereby opening up an area of tissue. Once a suitably sized area of tissue has been retracted, the retractable member 14a is then clamped by the securing mechanism 16a such that the retractable member 14a and the tissue hook 18a are held in a fixed position.

The underside 15a of the base 12a of the embodiment of the tissue retractor of FIG. 1A is sufficiently flexible such that it is capable of conforming to a surface to which it is attached to. In other words, the underside 15a is flexible in that it adopts the shape and contouring of the surface, which in this case is typically that of a human body, on which it is placed, and adheres to that surface.

Figure 1B:
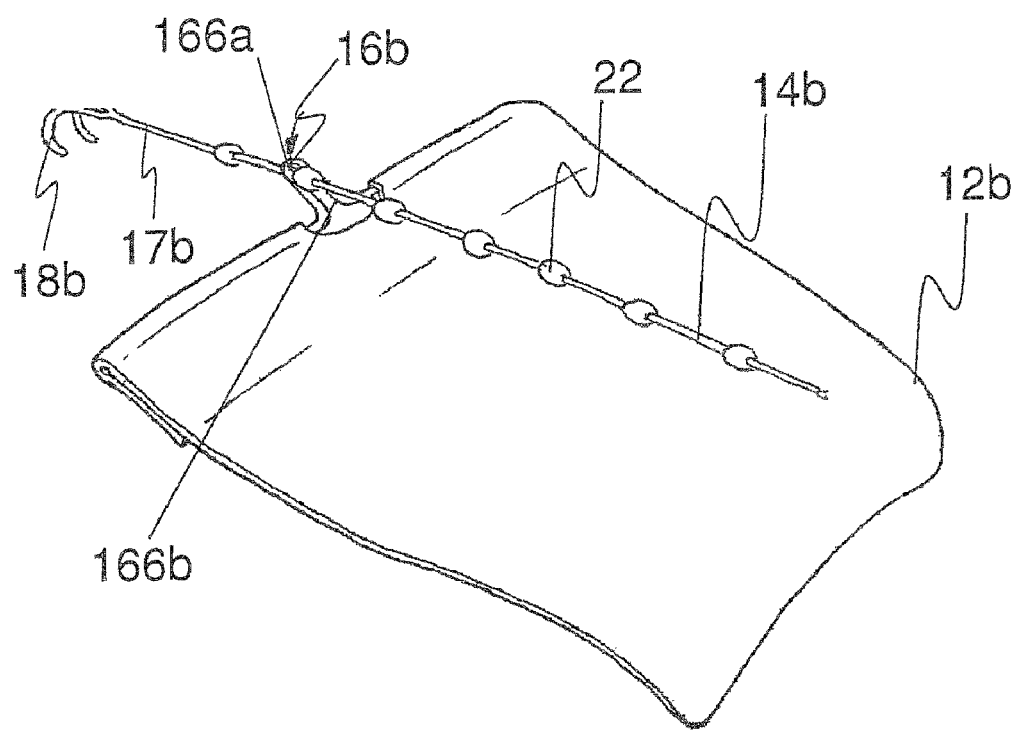

In another exemplary embodiment shown in FIG. 1B, the tissue retractor also includes a base support unit 12b having a securing mechanism 16b, a (double-ended) tissue hook 18b connected, via a mounting portion 17b, to a retractable member 14b. This retractable member 14b is inelastic in its central longitudinal axis and flexible in at least one axis deviating from said central longitudinal axis, and is connected (or coupled) to the tissue hook 18b. In FIG. 1B, the base support unit 12b is illustrated as a flexible adhesion pad or a drape that is removably attachable to a surface (typically a tissue or a limb) proximate to the incision (not shown). In this embodiment, the securing mechanism 16b is a metal wire bent in a teardrop shape, having a narrow end 166a and a wide end 166b. The wide end 166b of the teardrop shaped wire securing mechanism permits the knobs 22 to pass through but not the narrow end 166a.

The retracting member 14b, which is essentially a flexible rod-like structure that is inelastic in its central longitudinal axis and flexible in at least one axis deviating from said central longitudinal axis, includes a plurality of knobs 22 distributed along its length. The knobs 22 may be formed integrally with the retracting member 14b or slid across the retracting member 14b such that a predetermined distribution across the retracting member 14b is created. The mounting portion 17b may be integrally formed, as shown, with the rod-like structure 14b. Alternatively the mounting portion 17b may, as in the exemplary embodiment of FIG. 1A, be insertable, removably or otherwise, into the knob 22 nearest an end of the rod-like structure 14b. The mounting portion 17b, if integrally formed, may be made from the same material, such as plastic, which is used herein for the retractable member 14b for example.

Accordingly, when in use, the retracting member 14b, including its knobs 22 are withdrawn away from the incision via the wide end 166b of the teardrop shaped wire securing mechanism 16b until the tissue engaged to the tissue hook 18b is sufficiently retracted. At that point, the retractable member 14b is raised into the narrow end 166a of the teardrop shaped wire securing mechanism 16b. With the retracted tissue attempting to revert to its original relaxed state from its presently retracted state, a reaction force is exerted on the retractable member 14b directed towards the incision. However, due to the retractable member 14b being in the narrow end 166a of the teardrop shaped wire securing mechanism 16b, the retractable member 14b is prevented from moving towards the incision as the knob 22 is caught by said narrow end 166a.

Figure 1C:
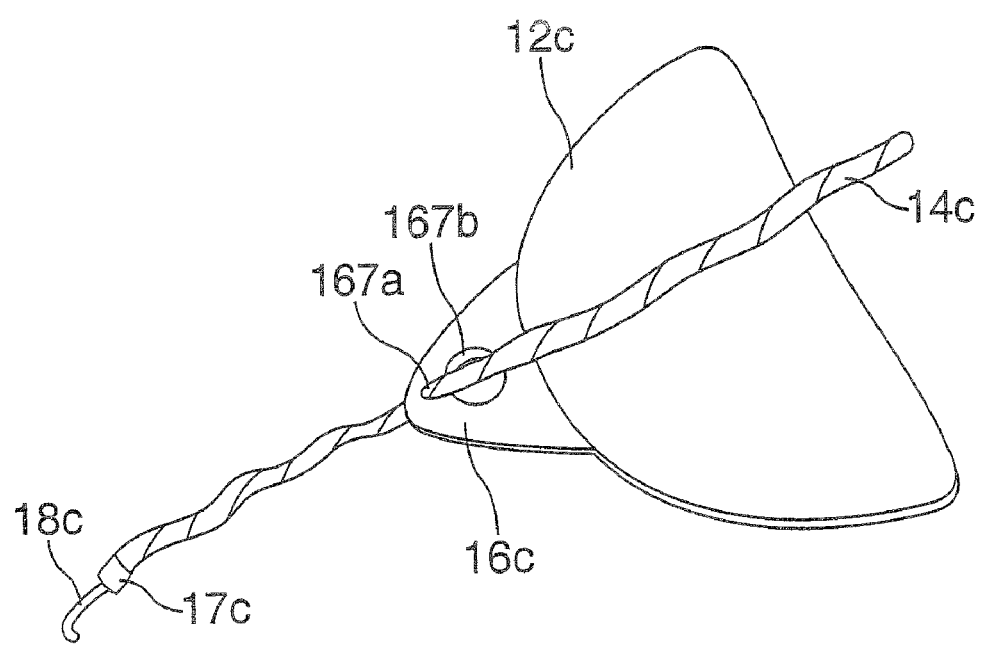

Similarly, the exemplary embodiment of FIG. 1C also includes a base support unit 12c having a securing mechanism 16c, a tissue hook 18c and a retractable member 14c that is inelastic in its central longitudinal axis and flexible in at least one axis deviating from said central longitudinal axis. The retractable member 14c may be a braided multi-strand wire (cable), or alternatively, may also be a belt or a strap made of plastic or a suitable fabric, for example. The retractable member 14e is connected (or coupled) to the (single-ended) tissue hook 18c via mounting portion 17c. In this exemplary embodiment, the base support unit 12c is a flexible thin pad having an adhesive underside (not shown). The securing mechanism 16c is also teardrop shaped with a wide end 167b and a narrow end (notch) 167a and the retractable member 14c is a cord. Essentially, the retractable member 14c may be, as mentioned, a cord, strip, strap, belt or any other suitable member that is substantially inelastic in its central longitudinal axis (i.e. it is not stretchable) and flexible in at least one axis that deviates from said central longitudinal axis. As in the previous exemplary embodiment of FIG. 1B, the retractable member 14c may be retracted up to a predetermined distance via the wide end 167b of the teardrop shaped securing mechanism 16c upon which, it may be secured by inserting and wedging the retractable member 14c into the narrow end (notch) 167a of the teardrop shaped securing mechanism 16c.

Figure 1D:
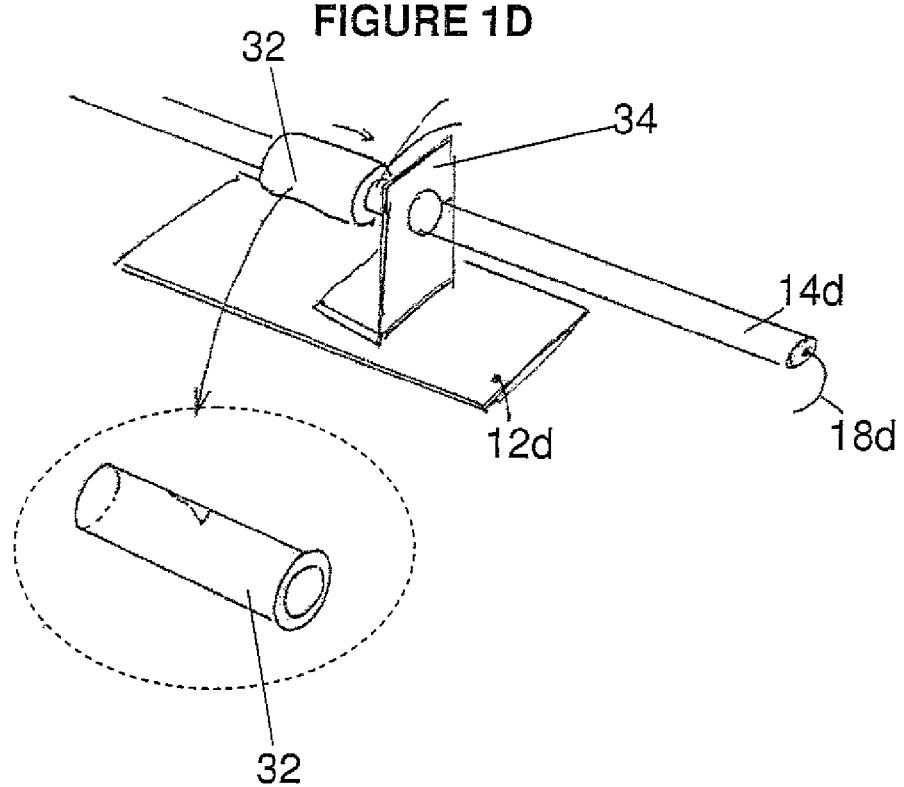

Referring to the exemplary embodiment of FIG. 1D, the tissue retractor thereof, as in the previous exemplary embodiments, includes a base support unit 12d, a retractable member 14d, a tissue hook 18d and a securing mechanism that includes a stopper 34 mounted on the topside 13d of the base support unit 12d, and a rotating body 32. The stopper 34 may be of any suitable shape and is illustrated as being substantially rectangular in the present embodiment. The position of the rotating body is always behind the stopper, i.e. further from an incision than the stopper 34, when in use. The tissue hook 18d may be attached to the retractable member 14d by any of the suitable mechanisms disclosed herein such as tight-fit means, form fit means and snap fit means, for example. The retractable member 14d may then be removably coupled to the rotating body 32 after being threaded through the stopper 34.

The rotating body 32 is slidably connected along retractable member 14d. The rotating body 32 may include a chuck mechanism and rotates between an open position and a closed position. In the open position, the chuck mechanism is correspondingly open and the retractable member 14 (a cord, a strip, a strap or a belt, for example) may freely slide through the rotating body 32 and stopper 34. Once the retractable member 14d is retracted to a predetermined distance, the rotating body 32 may be rotated into its closed position, which closes the chuck mechanism and locks the rotating body 32 onto a specific portion of the retractable member 14d.

If the tissue hook 18d is engaged with retracted tissue while the rotating body 32 is in the closed position, the stopper 34 prevents the rotating body 32, which is locked onto the retractable member 14d, from moving towards the incision, thereby maintaining the retracted state of said incised tissue.

Figure 1E:
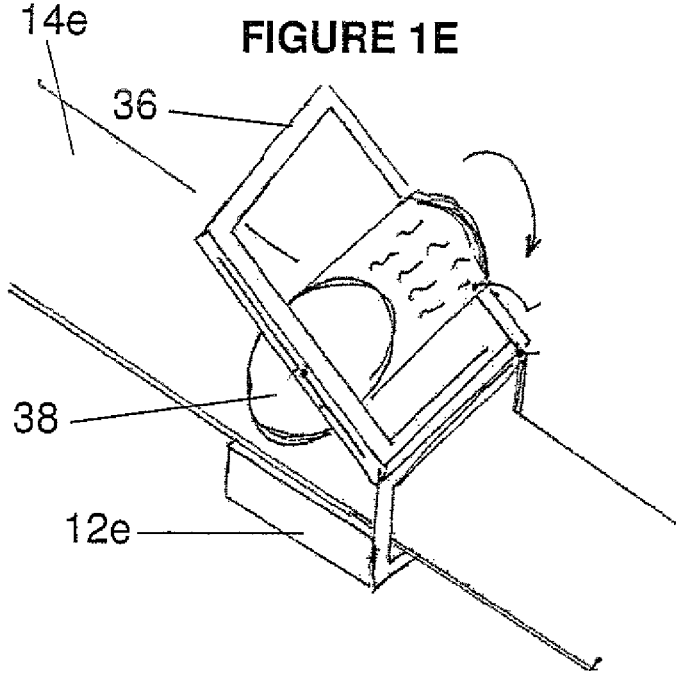

In FIG. 1E the exemplary embodiment of the tissue retractor differs from that of FIG. 1D with regard to its securing mechanism. The securing mechanism of the embodiment of FIG. 1E includes a roller 38 that is lockable by an engagement lever (or frame) 36. The engagement lever 36 is connected to the roller 38 along its central longitudinal axis of rotation and is pivoted about an axis parallel to said central longitudinal axis. Accordingly, in this embodiment, the retractable member 14e is typically a belt-like form and when the retractable member 14e is retracted away from an incision, the roller 38 rotates, about its longitudinal axis, in a clockwise direction. However, once the engagement lever 36 is closed downwards, the roller 38 is pressed, by the engagement lever 36, against the retractable member 14e with sufficient force such that the roller 38 prevents the retractable member 14e from rolling in an anti-clockwise direction, i.e. towards the incision, even if the retractable member is biased to do so.

The engagement lever 36 may be spring loaded such that it is biased towards being open upwards, i.e. in a release position such that the roller 38 may rotate freely. The engagement lever 36 may also include a catch that secures to the base support unit 12e when the engagement lever 36 is closed downwards.

Figure 1F:
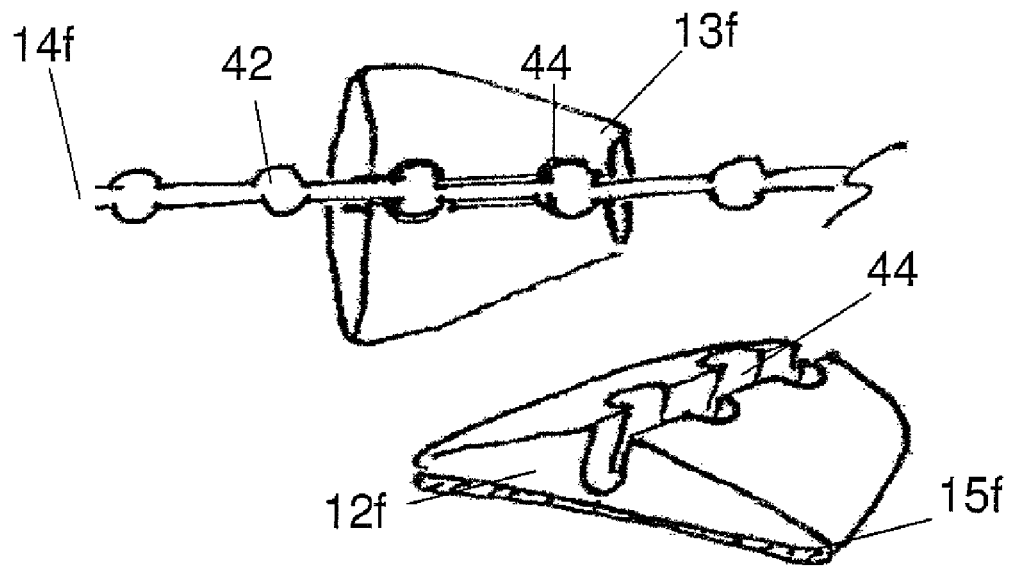

In FIG. 1F, an exemplary embodiment of a tissue retractor having a complementary securing mechanism is shown. In this embodiment, as in the embodiment of FIG. 1B, the retractable member 14f includes knobs 42 that may be integrally formed therewith or arranged thereon in a slidable manner. The topside 13f of the base support unit 12f comprises a molded surface having a plurality of crevices 44 that are complementary to the shape of the knobs 42. The crevices 44 are adapted to accommodate therein in a secure fit (or tight fit) manner, at least a selection of the knobs 42 of the retractable member. As shown, when the two knobs 42 are received by the complementary crevices 44, the position of the retractable member 14f is maintained with respect to base support unit 12f.

Figure 1G:
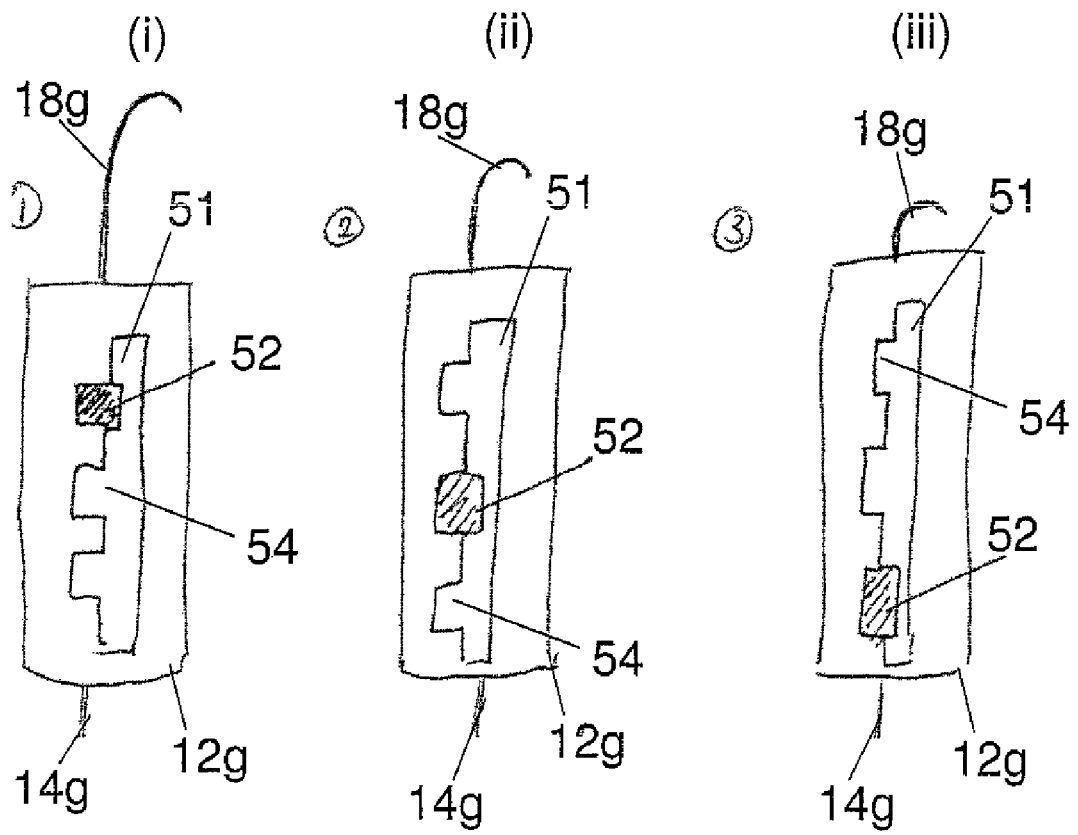
Figure 1H:
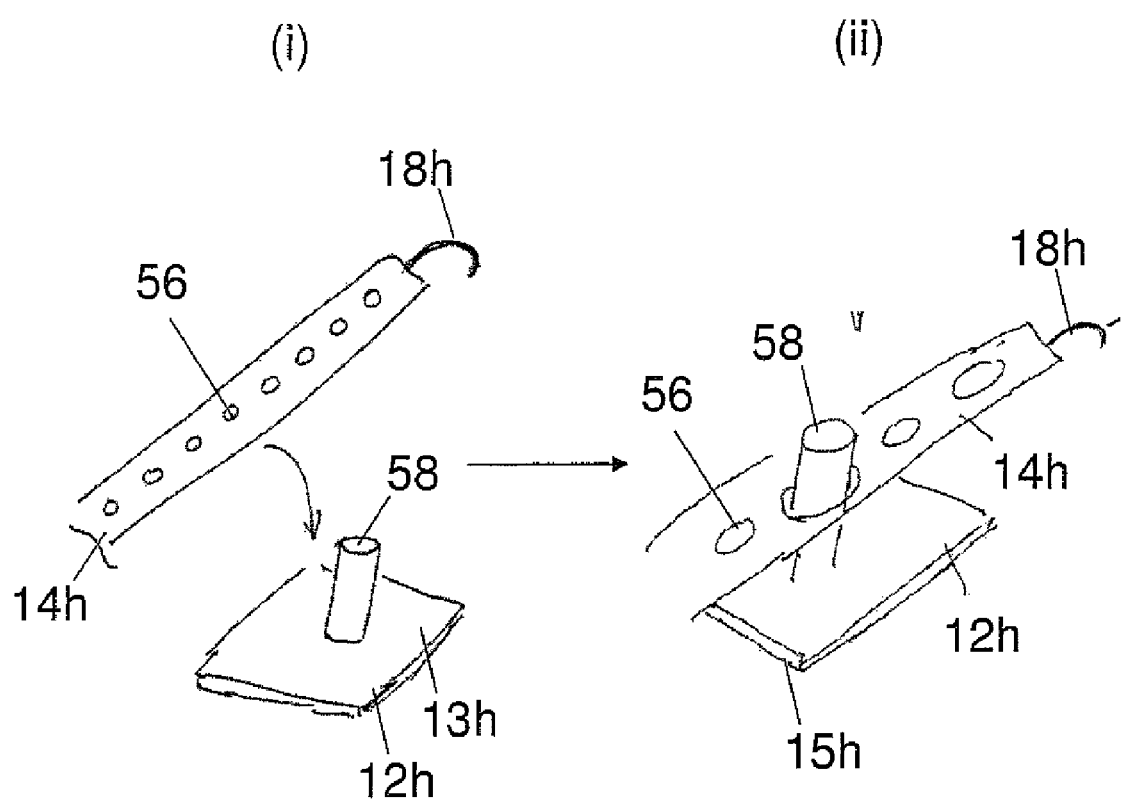

Exemplary embodiments illustrated in FIGS. 1G and 1H, utilize a similar slot 51 and 56 and pin 52 and 58 securing mechanism. In FIG. 1G a common slot 51 having a plurality of notches 54 is formed on the base support unit 12g. A corresponding pin 52, which may either be attached to the retractable member 14g or be an independent body, serves to secure the retractable member 14g to the base support unit 12g.

In the exemplary embodiment of FIG. 1G where the pin 52 is attached to the retractable member, either integrally or as a tight gripping clip, for example, the retractable member 14g is threaded through the base support unit such that the pin 52 slides freely along the slot 51. When the tissue hook 18g is engaged to tissue opened by an incision, the retractable member 14g is pulled away from the incision to retract the tissue to a predetermined distance. Typically, in this embodiment, where the pin is attached to the retractable member 14g, the distance that the retractable member 14g may be retracted is limited by the length of the slot 51.

In the alternative exemplary embodiment of FIGS. 1G (i)-1G (iii), where the pin 52 is an independent body, the retractable member 14g may still be threaded through the base 12g. In this embodiment when the retractable member 14g has been sufficiently retracted, the pin 52 may then be placed in the notch 54 to secure the retractable member 14g via a pin to a press-fit mechanism, for example. The pin 52, when secured to the retractable member 14g, may still move along the slot 51 should the tissue in question require additional retraction without having to remove the pin 52 and re-insert it as previously described. This is especially useful if the adjustments (additional retraction) required to the retractable member 14g are not significant and slight.

As illustrated in FIGS. 1G (i)-(iii), with each subsequent notch 54 in which the pin 52 is inserted into, the retractable member retracts by a greater distance, such that the tissue hook 18 is drawn nearer to the base support unit 12.

In FIG. 1H, the retractable member 14h includes a plurality of slots 56 or openings (through-holes) distributed along its length. The slots or openings 56 may be formed via punching out the required shape and sized slot or opening on a regular retractable member. The topside 13h of the base support member 12h includes a pin 58 having a diameter that may be slightly larger than the diameter of the slot 56. When in use, the pin 58 can provide for a tight and secure fit between the slot 56 and the pin 58.

Alternatively, the diameter of the pin 58 may be less than the diameter of the slot 56 thereby resulting in a loose fit, which can be easier for a surgeon, for example, to use during an operation.

FIGS. 2A and 2B illustrate an exemplary embodiment of a tissue retractor having a hook and loop fastener as a securing mechanism. With reference to these figures, the exemplary embodiment illustrated here, as in previous embodiments, includes a base support unit 12i having a topside 13i and an underside 15i. The topside 13i includes a securing mechanism 66, which removably secures a retractable member 14i to the base support unit 12i. The securing mechanism 66 may, for example, be an adhesive or (a part or a layer of) a hook and loop fastener. The underside 15i is adapted to be conformable to any surface that it is to be attached to. The tissue retractor also includes a tissue hook 18i, wherein the tissue hook 18i includes a tissue engagement portion 19i and a mounting portion 17i. The tissue hook 18i is connected to one end 201 of the retractable member 14i via the mounting portion 17i. The mounting portion 17i in FIG. 2A may be an extended elastomeric or rigid cord or tube, for example. Alternatively, in the embodiment illustrated in FIG. 2B, the mounting portion 17i may be a clip or clamp that secures directly to the end 201 of the retractable member 14i In this exemplary embodiment of FIGS. 2A and 2B, the retractable member 14i is a hook and loop fastener strip having an underside 200. Typically, a hook and loop fastener includes two layers namely a hook side and a loop side. Typically, the hook side comprises a fabric covered with plastic hooks and the loop side comprises plastic loops adapted to engage with the hook side. An example of a hook and loop fastener strip includes VELCRO® materials as originally described in U.S. Pat. No. 2,717,437, which is hereby incorporated by reference for all purposes.

In the exemplary embodiments of FIGS. 2A and 2B, the underside 200 of the retractable member 14i may be the hook side, while the securing mechanism 66 on the topside 13i of the base support unit 12i may be the loop side. Accordingly, and in line with the above description provided about hook and loop fasteners, the underside 200 has raised pile threads 9, the ends of which are hook shaped and ordinary raised pile threads 10 extending therefrom. Similarly the securing mechanism 66 on the topside 13i of the base support unit 12i also includes raised pile threads 9, the ends of which are hook shaped and ordinary raised pile threads 10, both of which may be considered to be loops, extending therefrom. When connected together, the raised pile threads 9 on the underside 200 of the retractable member 14i engage the pile threads 9 of the opposing face, i.e. the securing mechanism 66 located on the topside 13i of the base support unit 12i (see also U.S. Pat. No. 2,717,437 for a detailed description of the principle behind the hook and loop fastener mechanism).

Figure 2C:
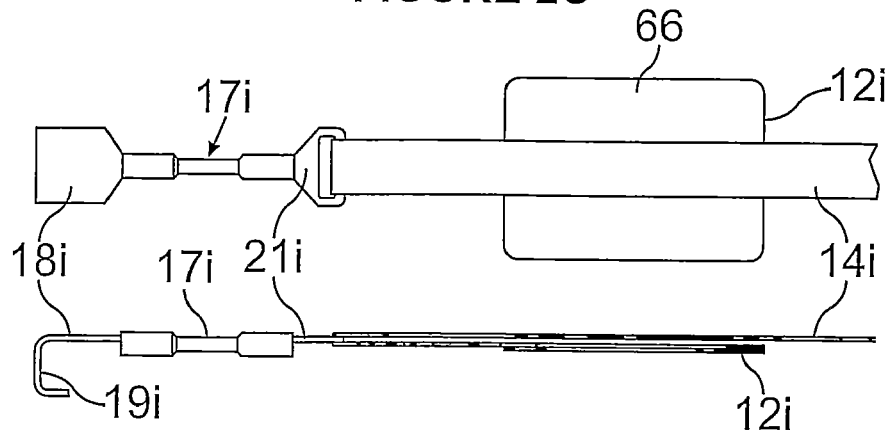
Figure 2D:
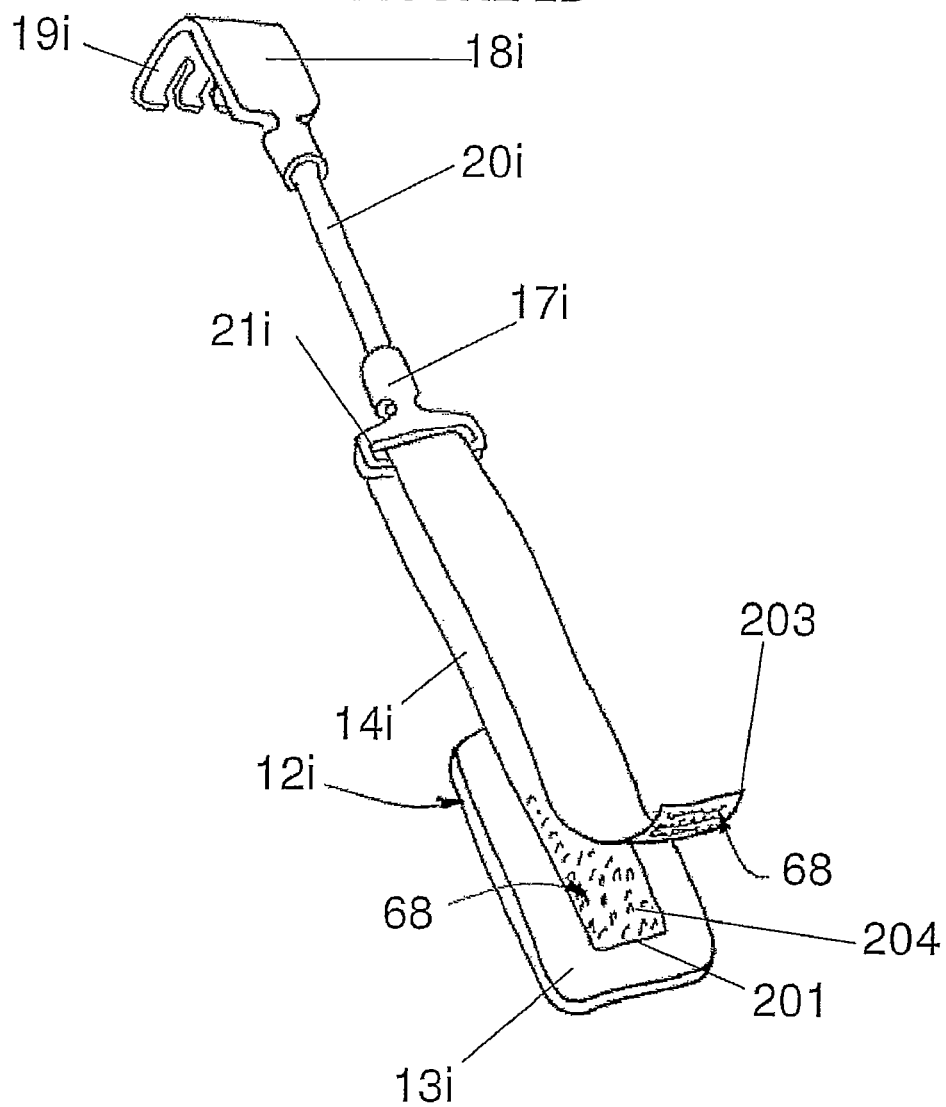

Referring to the mounting portion of the tissue hook, in another exemplary embodiment of the tissue retractor illustrated in FIGS. 2C and 2D, the mounting portion 17i thereof includes an aperture or slot 21i. The mounting portion 17i also includes a shock prevention element 20i. Turning to the securing mechanism of this embodiment, the first end 201 of the retractable member 14i is secured to the securing mechanism 66 (not visible) on the topside 13i of the base support unit 12i. A second end 203 is threaded through said aperture 21i and loops back to be removably attached to a facing side 204 of the retractable member 14i. The facing side 204 is proximate to the first end 201. The facing side 204 also includes an attaching mechanism 68 that attaches to a corresponding face of the looped back portion of the retractable member 14i. The term "looped back portion" refers to the retractable member 14i that passes through the aperture 21i. Accordingly, the looped back portion of the retractable member 14i may also include a complementary attaching mechanism adapted to removably attach to attaching mechanism 68. Attaching mechanism 68 may be any one of a hook and loop fastener, as previously described, or a adhesive, for example.

While the retractable member of the embodiments of FIGS. 2A and 2D is formed as a hook and loop fastener strip with its entire underside 200 comprising a part of or a layer of a hook and loop fastener, the retractable member of the embodiment of FIGS. 2C and 2D is an illustration of an embodiment wherein only at least one portion of the retractable member comprises a part of or a layer of a hook and loop fastener.

Reverting to the mounting portion of FIGS. 2C and 2D, the shock prevention element 20i is typically elastomeric and as illustrated, the shock prevention element 20i can be an elastomeric tube. The shock prevention element 20i serves the purpose of providing a greater degree of flexibility to the mounting portion 17i. A completely rigid system (which is also considered as part of the present invention) may possibly impart, inadvertently, injury to the tissue being retracted. Examples of elastomeric materials that may be used in fabricating the shock prevention tube 20i include, but are not limited to, latex rubber, silicone runner and thermoplastics, such as polyvinylchloride (PVC), for example.

In an alternative exemplary embodiment (not illustrated in a figure), the mounting portion 17i may include two sub-portions. The first sub-portion may be the shock prevention element 20i attached to the tissue hook 17i followed by the second sub-portion that includes the aperture 21i. In this alternative exemplary embodiment, instead of an elastomeric tube, the shock prevention element 20i may simply be a shock prevention cord that is also elastomeric, for example.

The surface of the topside 13i is adapted to secure a hook or a loop fastener strip and may include a shape selected from the group consisting of a continuous strip, a discrete element and a combination thereof. The surface shape of the at least one continuous fastener strip and the at least one discrete element is selected from the group consisting of rectangular shapes, triangular shapes, elliptical shapes and any combination thereof.

FIG. 2D is a perspective view of the exemplary embodiment of FIG. 2C. In the embodiment of FIG. 2D, one end portion of the hook and loop fastener 14i is attached to the topside 13i of the base support unit 12i. This end portion of the hook and loop fastener 14i has on its surface, opposite the topside, a securing mechanism 66 adapted to secure a hook and loop fastener strip 14i also having a corresponding securing mechanism 66. In other words, the securing mechanism 66 attached to the topside 13i of the base 12i is complementary to the securing mechanism 66 located on the hook and loop fastener strip 14i. In this particular embodiment, it should also be noted that the means of securing the hook and loop fastener strip 14i to the base 12i may also be by way of hook and loop fasteners. Alternatively, the hook and loop fastener strip 14i may be bonded to the base 12i using adhesives or thermal bonding, for example.

Figure 3A:
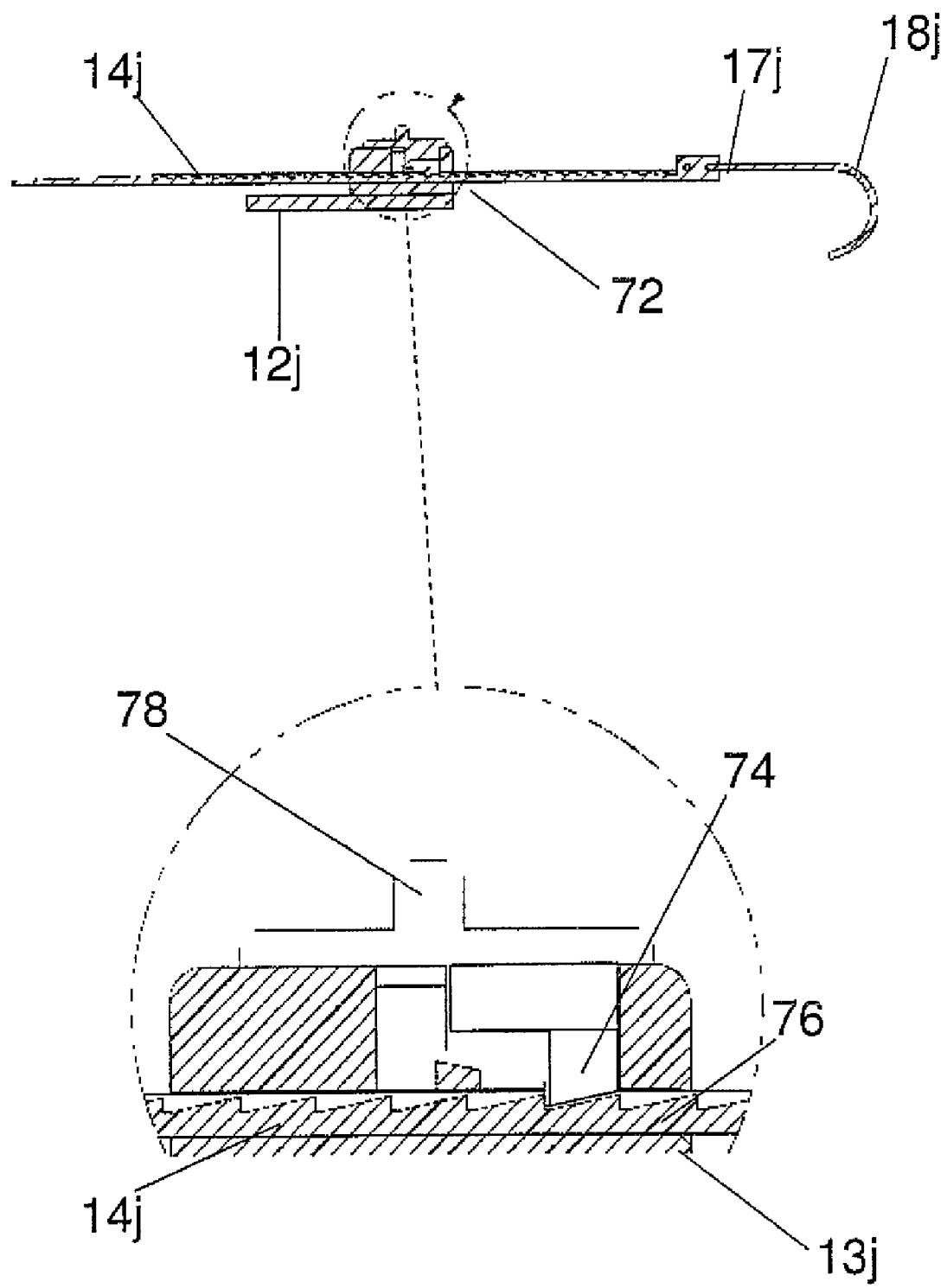
FIGS. 3A-3E illustrate exemplary embodiments of tissue retractors including ratchets.

FIGS. 3A-3E illustrate exemplary embodiments of various ratchetable tissue retractors. In the embodiment of FIG. 3A, the retractable member 14j is a plastic strap that includes a plurality of ratchet teeth 76 arranged along its longitudinal axis. The plastic strap 14j is securable to the topside 13j of the base support unit 12j via securing mechanism 72. The plastic strap is connected to a tissue hook 18j via its mounting portion 17j. Securing mechanism 72 on the topside 13j of the base support unit 12j includes a releasable pawl 74, which is made releasable by a push-button 78. An example of such straps having a releasable securing mechanism as described above is disclosed in U.S. Pat. No. 6,185,791, which is hereby incorporated by reference for all purposes.

In the embodiment of FIG. 3A, the push-button 78, when depressed, actuates the pawl 74 in an upward direction and out of the recesses formed between the ratchet teeth 76. This allows the plastic strap 14j to be moveable, i.e. to be retracted away from, or moved towards an incision. Upon release of the push-button 78, the pawl 74 moves downwards to its default position and slides into the nearest recess between two ratchet teeth 76 nearest thereto, thereby engaging and retaining the plastic strap 14j in its current position.

As mentioned earlier, the plurality of ratchet teeth 76 of the plastic strap 14j is adapted to releasably engage with the releasable pawl 74 as the plastic strap is retracted away from the incision. In other words, the plastic strap 14j may only retract or move in one direction, this direction being away from the incised tissue while the releasable pawl 74 is engaged. When the push-button 78 is actuated, the releasable pawl 74 is released (or disengaged) in the manner as previously described, and the plastic strap 14j may then move in a second direction opposite to the first. More specifically, in one non-limiting implementation, when medical personnel, such as a surgeon, for example, retracts tissue, the ratchet teeth 76 are drawn past the releasable pawl 74, regardless whether the pawl is in its engaged or released position. Once the retraction of the retractable member 14 stops, the pawl drops into a recess defined between two of the nearest ratchet teeth 76 to provide an immovable engagement to the plastic strap 14j until such time as the pawl 74 is lifted out of the recess and therefore, removed from engagement with the ratchet teeth 76, via actuation of the push-button 78.

Figure 3B:
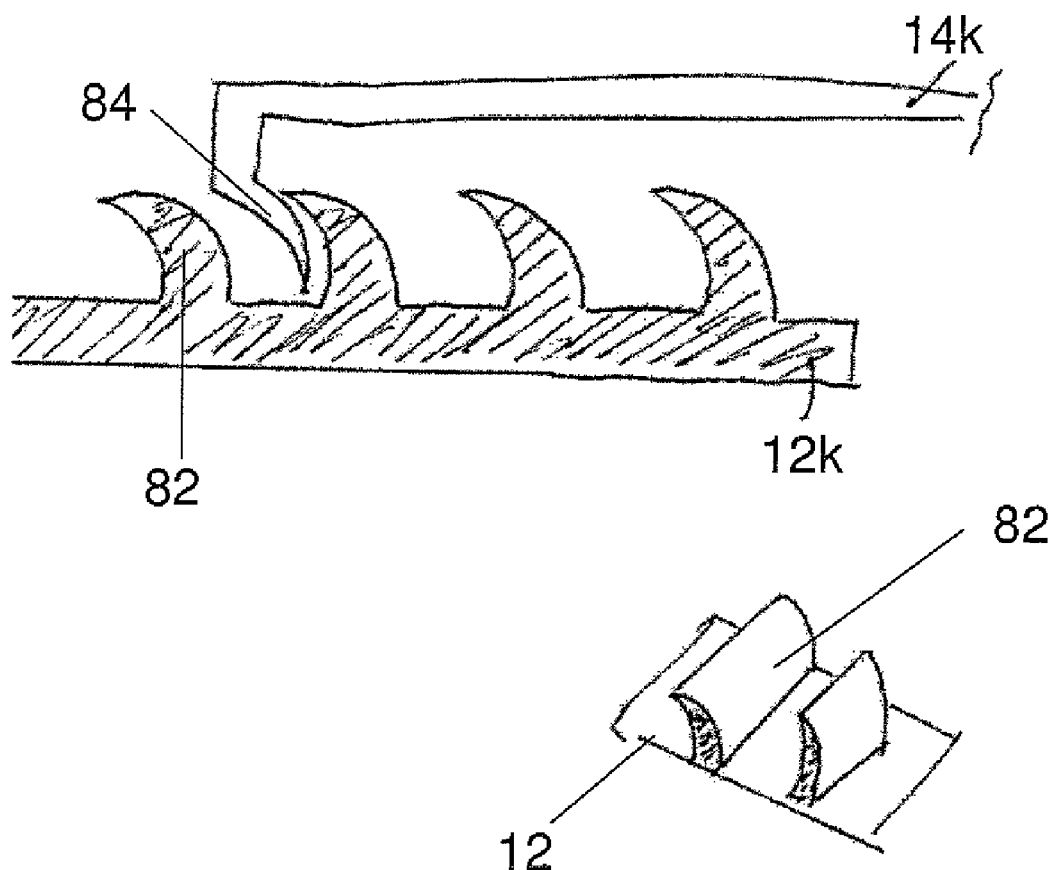

In this context it is to be noted that a ratchetable tissue retractor is taken to be one that includes a pawl (either mounted on the topside of the base support unit or on the retractable member) working in combination with ratchet teeth, mounted to correspond to said pawl. This allows for motion in one direction only, unless said pawl is released. In this respect, FIGS. 3B-3E illustrate other various embodiments of ratchetable tissue retractors according to the aforesaid definition. In FIG. 3B the retractable member 14k includes a pawl 84 that engages the ratcheted teeth 82 of the base support unit 12k. In this embodiment, the shape of the pawl 84 and the shape of the ratchet teeth 82 each have a curvature of a fixed radius such that the curvature of the pawl 84 corresponds to that of the ratchet teeth 82 thereby ensuring complementary mating surfaces between said pawl 84 and ratchet teeth 82.

Figure 3C:
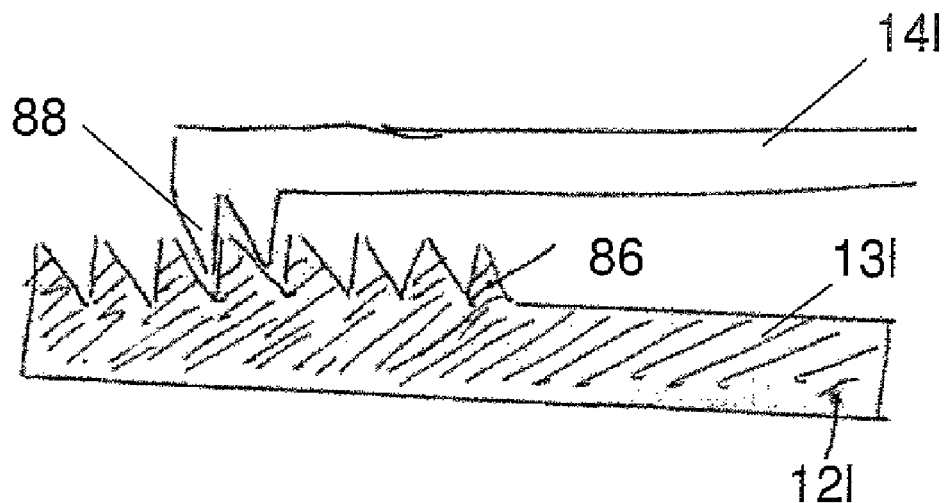
Figure 3D:
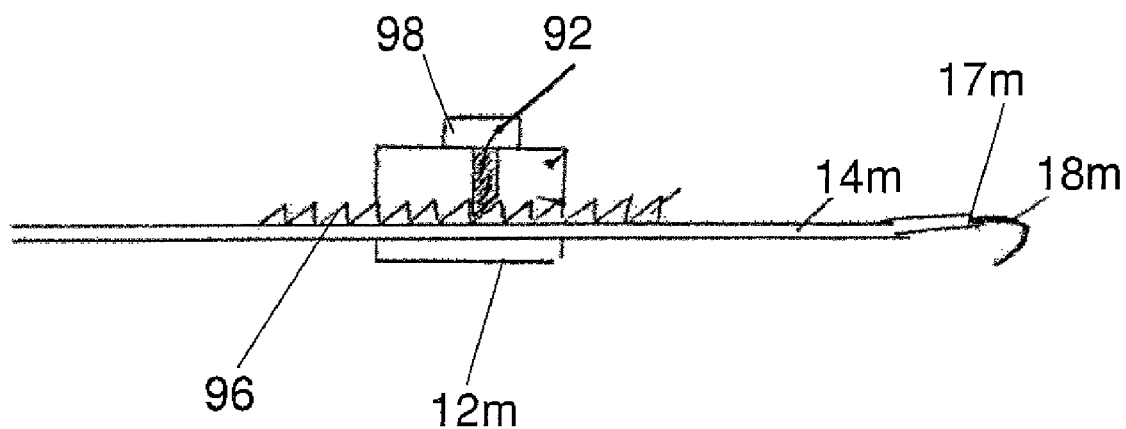
Figure 3E:
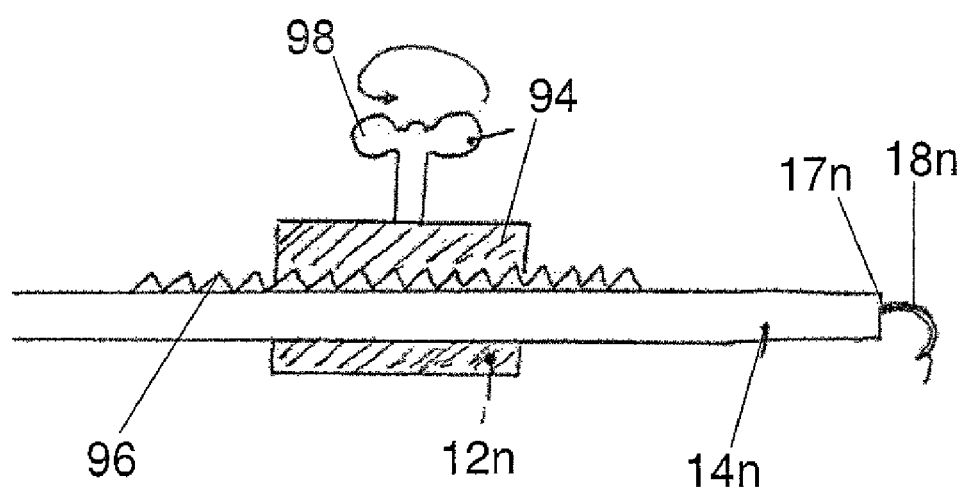

In FIGS. 3C-3E, the ratchet teeth are all saw-tooth in shape. Accordingly, the corresponding pawls are also saw tooth in shape. Referring to FIG. 3C, as in FIG. 3B, the pawl 88 is located on the retractable member 14l and the ratchet teeth 86 are located on the topside 13l of the base support unit 12l. In FIGS. 3D and 3E, the ratchet teeth 96 are located on retractable member 14m and 14n. The base support units 12m and 12n of the respective tissue retractors of FIGS. 3D and 3E each have clamps 98 that engage a singular pawl 92 or a plurality of pawls 94 when actuated. The actuation of the pawls 92 and 94 may be a twisting motion, a screwing motion, a pressing motion or any combination thereof that results in the pawls 92 and 94 engaging their respective ratchet teeth 96, as described earlier.

In the embodiments of FIG. 3A-3E, the tissue hook may be attached to the plastic strap in several ways. In the exemplary embodiment of FIG. 3A, the tissue hook 13j may be attached directly, via its mounting portion 17j to the plastic strap 14j. In this embodiment, the mounting portion 17j may simply be a sleeve that is a form-fit or a snap-fit over an end of the plastic strap. In another exemplary embodiment illustrated in FIG. 2D, the mounting portion 17i may include two sub-portions 20i and 21i. The first sub-portion 20i may be a cord attached to the tissue hook 18i followed by the second sub-portion 21i that includes an aperture that fits onto the plastic strap 14i as described above. As a further alternative, any of the other methods and devices for mounting the tissue hook onto the retractable member, as described herein, may also be implemented.

At this juncture, it should be noted that any suitable tissue hook may be used in conjunction with any of the various exemplary embodiments of the tissue retractor of the present invention. It is also to be understood that the term "tissue hook" also includes tissue hooks having one, two three or four claws (fingers) or even a solid claw. In this respect the exemplary embodiments of tissue refractors shown in FIGS. 1A, 1B, 2D and 2C have one, two, three claws and a solid claw, respectively. Further examples of tissue hooks include, but are not limited to, Tyrell delicate prong hook, Gillies skin hook, Kilner hooks and two-pronged Joseph hooks having prongs that vary between about 2 mm-10 mm in length. In addition, the term "tissue hooks" also includes the tissue engagement portions of commercially available Fomon retractors, Rake retractors and Desmarres retractors, for example. Similarly, the mounting portion of the tissue hook that is connected, coupled to or received by the retractable member may also take on many forms and is typically dependent upon the type of retractable member used.

Figure 4A:
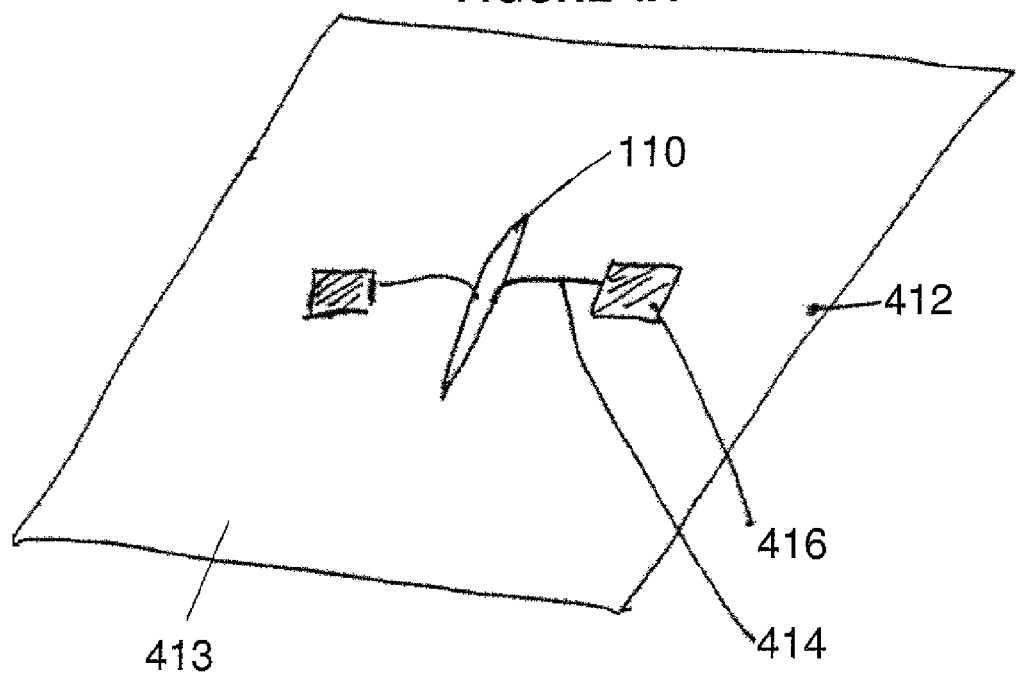
FIGS. 4A-4D illustrate various exemplary embodiments of base support units capable of having a plurality of retractable members.

FIGS. 4A-4D illustrate further exemplary embodiments of base support units of tissue retractors for retracting tissue opened by an incision. In FIG. 4A, the base support unit 412 is a sheet-like structure having a topside 413 and an underside being adapted to be conformable and to be removably attachable to a surface proximate to the incision. The topside 413 of the base support unit 412 is adapted to form an opening 110, which extends from the topside 413 through to the underside (not shown). The opening 110 surrounds the incision thereby providing access to the tissue surface opened by said incision beneath the base support unit 412. The base support unit 412 further includes at least one securing mechanism 416, typically removably attachable to the topside. In the embodiment of FIG. 4A, any portion of the topside of the base support unit 412 may be suitable for attaching the securing mechanism 416 to. However, depending on operational requirements, it may be most suitable to have the securing mechanism 416 arranged proximate to the opening 110.

The opening 110 may be formed by at least one of a perforation or a cut-out that extends from the topside 413 through to the underside of the base support unit 412. As also shown in FIG. 4A, a pair of retractable members 414, engaged with an opened tissue, via opening 110, is attached to a corresponding pair of securing mechanisms 416.

As an illustrative example, the retractable member 414 used in conjunction with the base support unit of FIG. 4A may be a hook or loop strap as described with respect to FIGS. 2A-2D above. Accordingly, in this exemplary embodiment, the securing mechanism 416 attached to the topside of the base support unit 412 is adapted to secure the hook or loop strap 414.

In an alternative illustrative example, the retractable member may be a plastic strap having a plurality of ratchet teeth, as in the embodiments of FIGS. 3A-3E. Correspondingly, the securing mechanism 416 attached to the topside 413 then includes a releasable pawl, wherein the plastic strap is adapted to releasably engage the pawl as the plastic strap is retracted away from the incision.

In one embodiment of the tissue retractor, the base support unit 412 may be a clear incision drape. Essentially, incision drapes are medical grade plastic sheets, with adhesives typically underside thereof for attachment to skin, that provide a sterile environment around the edge of any tissue opened by an incision. The incision drape may include antimicrobial properties and adheres securely to the wound edge and is also adapted to conform to body contours and stretches to allow limb manipulation. Incision drapes are commercially available and examples thereof include IOBAN™ and LOBAN™ from 3M™.

Figure 4B:
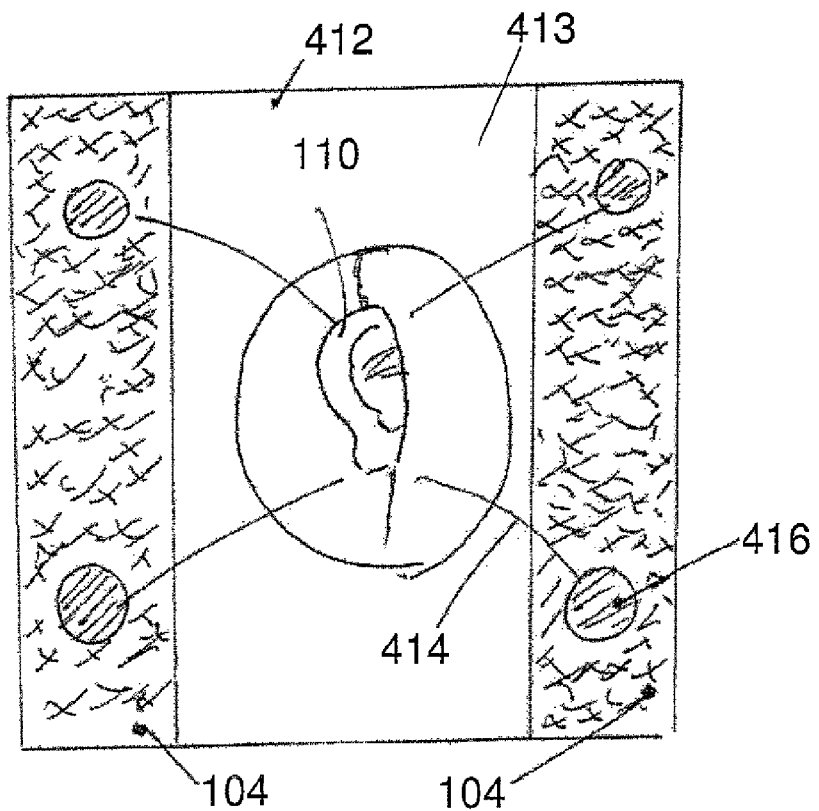

FIG. 4B is an exemplary embodiment of base support unit 412 (an incision drape) having an opening 110 in its central region through which access it provided to tissue on which a surgical procedure is to be performed. The topside 413 of the base support unit 412 includes a securing mechanism 104 having a surface adapted to secure a hook or loop fastener strip. As shown, the securing mechanism 104 is elongated and lies along the entire length of two opposite sides of said base support unit 412. This provides the surgeon with the flexibility to retract said retractable member 414, which includes a complementary securing mechanism 416 thereon, and to secure it to any position along said securing mechanisms 104. In this embodiment, the base support unit 412 and its corresponding securing mechanisms 104 may secure a plurality of retractable members 414 via their complementary securing mechanisms 416.

Figure 4C:
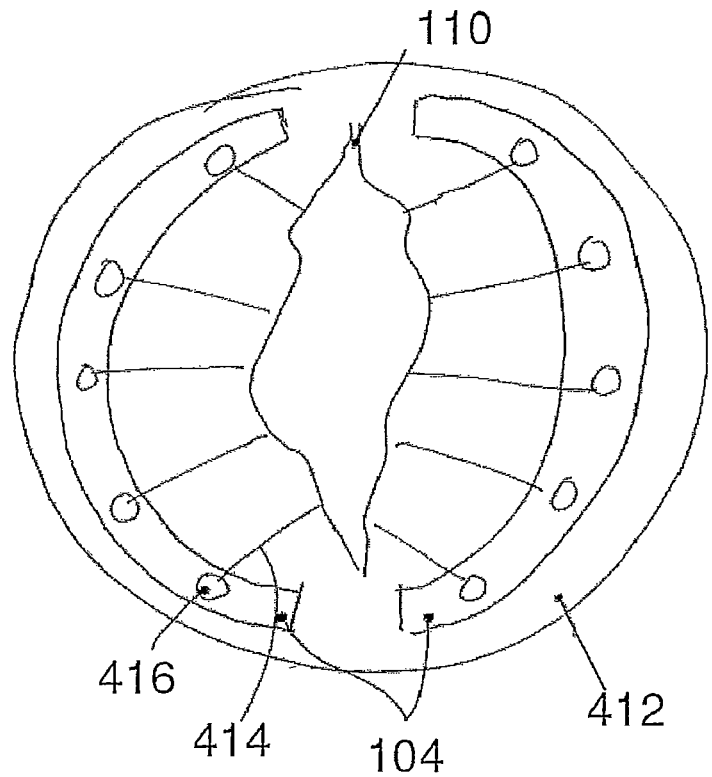

In FIG. 4C, the base support unit 412 is circular in shape. Accordingly, the securing mechanism 104 follows, substantially, the shape of the periphery of the base support unit 412 in that the securing mechanism 104 is a substantially semicircular. As in the embodiments of FIGS. 4A and 4B, a pair of securing mechanisms 104 is placed along the periphery of the topside of the base support unit 412. As above, this provides the surgeon with the flexibility to retract said retractable member 414, or a plurality thereof (a hook or loop fastener strip), and to secure it to any position along said securing mechanisms 104.

Figure 4D:
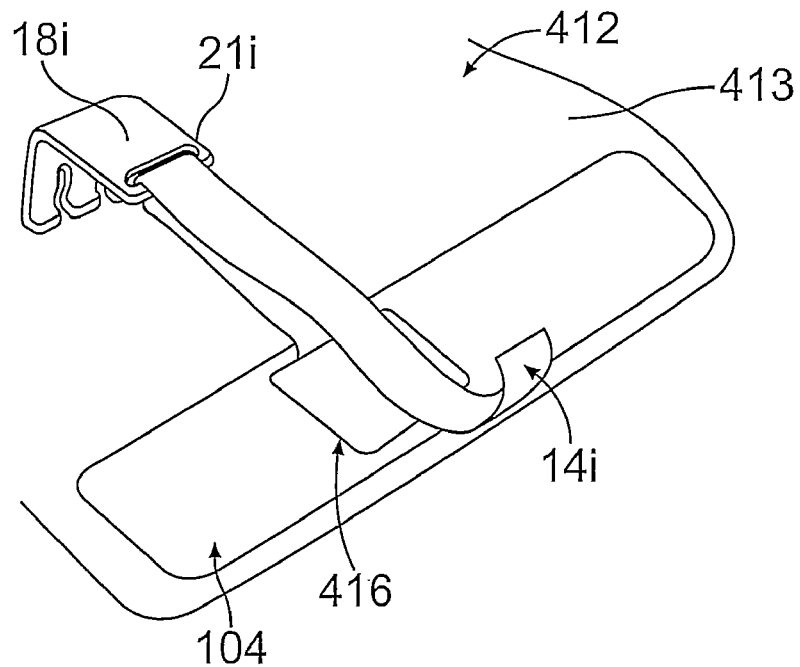

FIG. 4D shows an exemplary embodiment of a base support unit 412 (an incision drape), that is a variation of the base support unit 12i of FIG. 2D, having an opening (not shown) in its central region through which access is provided to tissue on which a surgical procedure is to be performed. The topside 413 of the base support unit 412 includes a securing mechanism 104 having a surface adapted to secure a hook and loop fastener strip. As shown, the securing mechanism 104 is elongated and lies substantially along the entire length of a side of said base support unit 412, much like the exemplary embodiment of FIG. 4B. Accordingly, there may be a corresponding securing mechanism 104 on the opposite length of the base support unit 412 (not shown). Securing mechanism 104 may be integrally formed with base support unit 412 or individually attached thereon by a user such as medical personnel like a surgeon, for example, in desired or appropriate locations on the topside 413 of the base support unit 12.

In this embodiment of FIG. 4D, a second securing mechanism 416 is placed on the initial (or first) securing mechanism 104. The securing mechanism 416 may be integrally formed with the retractable member 14i, which is described earlier with respect to FIG. 2D. This embodiment provides a user, such as a surgeon, with the flexibility to retract said retractable member 14i, and to secure it to the securing mechanism 416. Alternatively, the retractable member 14i may be attached to any position along said securing mechanisms 104. Where the securing mechanism 416 is integrally formed with the retractable member 14i, the securing mechanism 416 includes on either of its planar surfaces either hook or loop fasteners in order that it can be attached, via one surface, to the base support unit 412 and secure, via its other surface, the retractable member 14i.

The underside of the base support units in any of FIGS. 4A-4D (or incision drape) is typically adapted to be removably attachable to the surface of the tissue to be opened by any incision. The attachment may be carried out using a medical grade adhesive, for example. In this respect, the medical grade adhesive can be selected from the group consisting of acrylic adhesives, silicone-based adhesives, urethane adhesives, synthetic rubber adhesives and natural rubber adhesives, for example.

Figure 5:
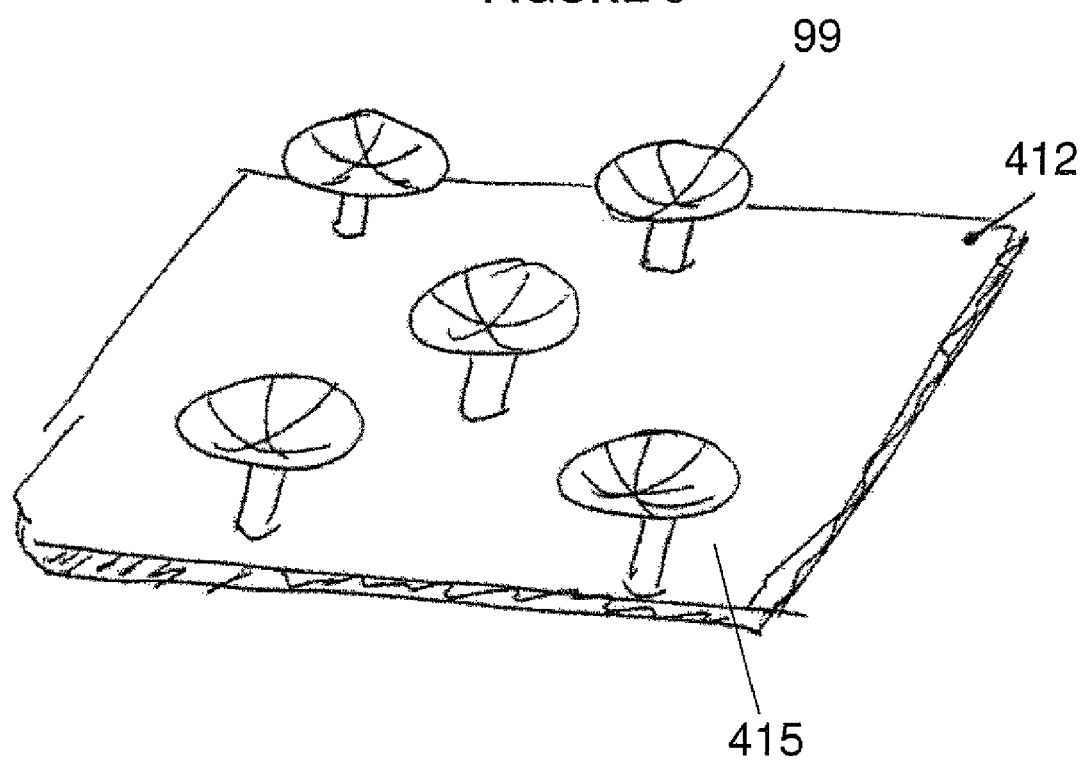
FIG. 5 illustrates an exemplary embodiment of a base support unit.

In an alternative embodiment, the underside of the base support unit may also be adapted to be removably attachable to said surface using suction cups as illustrated in FIG. 5. In this embodiment, the base support unit 412 includes at least one (vacuum) suction cup 99 on its underside 415.

In another embodiment, the base support unit, securing mechanism, tissue hook and retractable member, as described in any of the previous embodiments, may each be individual components of a surgical kit. In this respect, the base support unit may simply be an incision drape on which a surgeon may pre-place, where necessary, the required securing mechanisms onto the topside of said base support unit. Following that, the surgeon may then proceed to use a retracting member having a tissue hook attached at an end thereof and removably secure said retracting member to the pre-placed securing mechanisms.

Figure 6A:
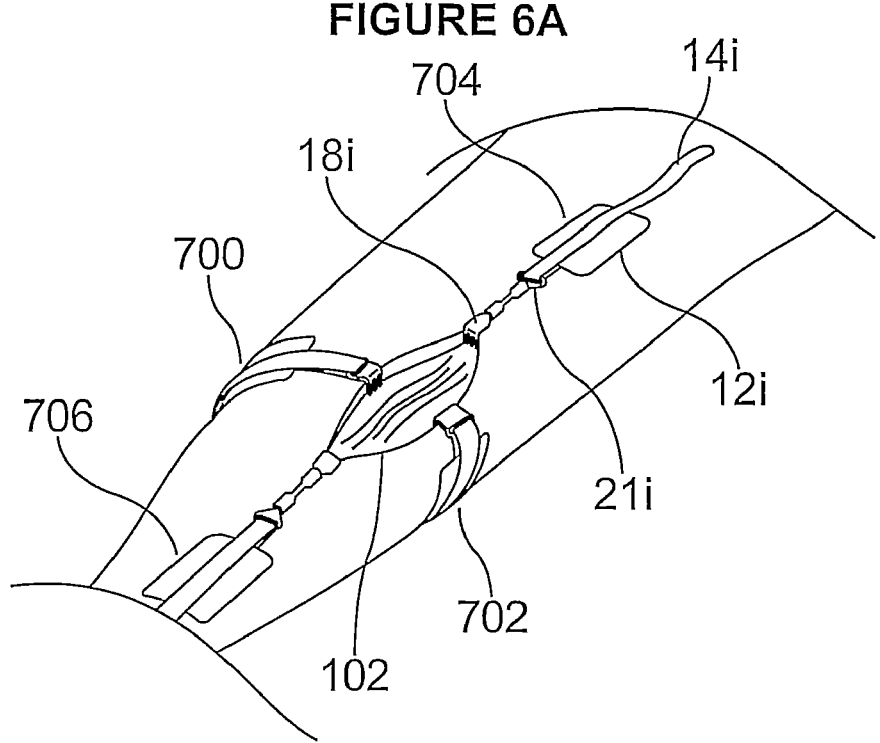
FIGS. 6A-6B illustrate exemplary embodiments of tissue retractors in use.

FIG. 6A illustrates the use of the embodiment of FIG. 2C or 2D in a surgical procedure. An incision 102 opens the tissue as shown. Four tissue retractors 700, 702, 704 and 706 are used with two of the tissue retractors 704 and 706 being situated along the axis of the incision 102. In other words, the base support unit 12i (shown in FIG. 2C or 2D) associated with tissue retractors 704 and 706 is attached such that the securing mechanism 66 (not visible as it is located beneath the retractable member 12i) on the topside 13i of the base support unit 12i is at least substantially parallel and along the axis of the incision 102. The remaining two tissue retractors 700 and 702 are situated approximately along an axis lateral (perpendicular) and midway to the axis of the incision 102.

In this embodiment, the base support unit 12i is attached on the tissue surface proximate to the incision 102. The topside 13i of the base support unit 12i includes a securing mechanism 66 (not visible) that is adapted to secure any one of a hook and loop fastener strap 14i. The underside of said base support unit 12i is adapted to be conformable and to be removably attachable to a surface of the skin proximate to the incision 102 as shown. As described in relation to FIGS. 2C and 2D, one end 201 of the strap 14i is attached to the base support unit 12i, via securing mechanism 66 (not visible). The remaining length of the hook or loop strap 14i is then used to connect to the mounting portion 17i of the tissue hook 18i.

The tissue hook 18*i* has a tissue engagement portion 19*i* and a mounting portion 17*i*. In this embodiment, the tissue engagement portion 19*i* is shown to be engaging a portion of the periphery of the tissue, along the axis of the incision 102. Also in this embodiment of the tissue retractor, the mounting portion 17*i* of the tissue hook 18*i* includes two sub-portions. The first sub-portion 17*i* is attached to the tissue hook 18*i* and may be a shock prevention cord (or shock prevention tube) of a fixed length or elastomeric in nature. The second sub-portion is an aperture or a slot 21*i* through which the second end 203 of the strap 14*i* passes through and then loops back such that the looped back portion is removably secured to the attaching mechanism 68 of its facing side 204 of the strap 14*i*.

Once the tissue retractor is setup in position, the remaining length of the 14*i* is retracted away from the engaged portion of the tissue opened by incision 102 as needed. The retraction may typically be such that the tissue engagement portion of the tissue hook 18*i* retracts the engaged portion of the tissue to a predetermined distance.

It should be noted that apart from using a hook or loop strap 14, and its associated securing mechanism, any other suitable retractable member and securing mechanism may be used to carry out the exemplary surgical procedure described above. In this respect, the securing mechanism may include a pawl and the retractable member may include a plastic strap having a plurality of ratchet teeth adapted to releasably engage the pawl, as described earlier with respect to FIGS. 3A-3E for example. It should also be noted that the base support unit may be any one of the exemplary embodiments described with respect to FIGS. 4A-4D and FIG. 5. In a case where the embodiments of FIGS. 4A-4D are used, generally, the base support unit should be positioned such that the opening surrounds the incision 102 and provides access to the tissue surface beneath the base support unit. Subsequently, as described above, at least one securing mechanism may be then attached onto the topside of the base support units of FIGS. 4A-4D.

A further alternative in the above surgical setup may be the use of the base support units described in relation to FIGS. 4A-4D, for example. In this respect, the opening of the base support unit may be positioned over the incised tissue and the underside of the base support unit adhered to the limb of the patient. Subsequently, a plurality of securing mechanisms may be placed at suitable locations on the topside of said base support unit. Following the placement of the securing mechanisms, the retractable members having tissue hooks connected thereto ca engage the incised tissue and retract said incised tissue to open it up as shown in FIG. 6A. Once sufficiently retracted, the retractable members are secured to the respective securing mechanisms.

Figure 6B:
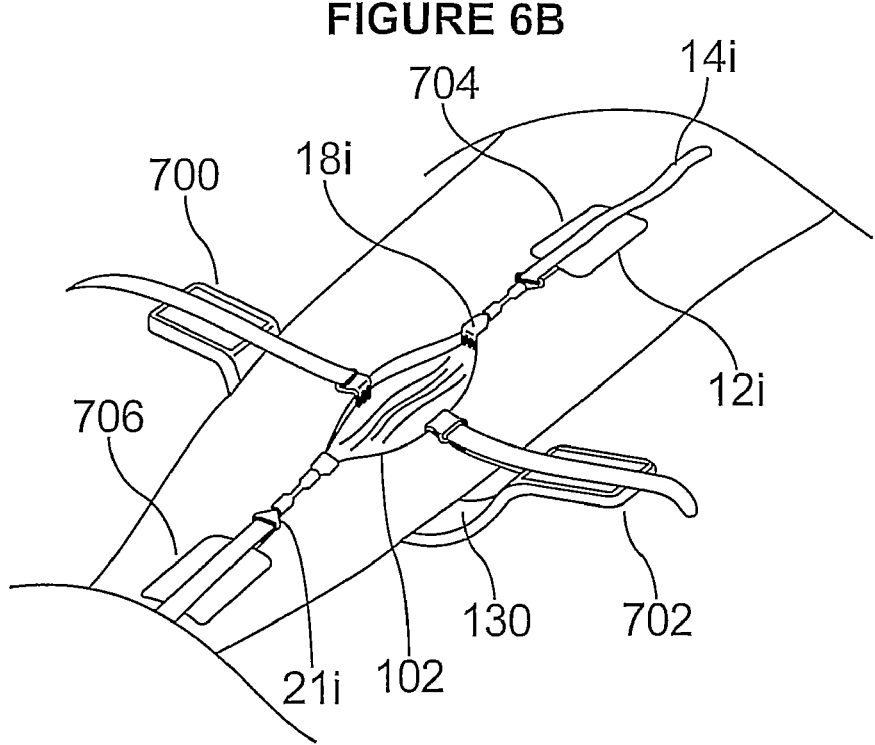

FIG. 6B is similar to the exemplary surgical use illustrated in FIG. 6A. The only difference in this exemplary use and that as described above, is that an additional support frame 130 is used to provide a surface on which the base support units 12 associated with tissue retractors 700 and 702 are attached to. As illustrated, the weight of the limb of the patient rests and holds the additional support frame 130 in place. The arrangement of the tissue retractors 700 and 702, position wise, is similar to that illustrated in FIG. 6A. As mentioned above, a base support unit described in relation to FIGS. 4A-4D may also be used in conjunction with said additional support frame 130.

The surgical setup illustrated in FIG. 6B may be used in the case where the limb of the patient does not provide an adequate surface area for all the required tissue retractors to be attached thereon. This may be the case with a child's limb, which is typically much smaller than an adult's limb, for example. The additional support frame 130 also serves to alter the direction of the retraction to provide some amount of lift (as in the retractors are positions at a higher level than the limb) in order to provide improved subcutaneous visibility.

In the aforesaid embodiments of the tissue retractor, it is to be noted that the tissue retractor is compact meaning that the overall profile of it is typically low, relatively flat and close to the tissue surface undergoing retraction. This compact construction of the tissue retractor is advantageous as it allows medical personal involved in the treatment of a patient to work without any hindrance from projecting structures, for example. Another advantage of the compact construction is that the tissue retractor is highly portable as well. Yet another advantage of the tissue retractor lies in its various components that are capable of being disassembled. This allows for an interchangeability and interoperability of components to suit the procedure being carried out.

The interchangeability and interoperability of components of the tissue retractor of the present invention permits it to be packaged as a kit. In one embodiment of the kit, said kit includes at least one base support unit having a topside and an underside. The underside of the base support unit is adapted to be conformable and to be removably attachable to a surface proximate to an incision.

The base support unit is adapted to form an opening, which extends from the topside through to the underside thereof. The opening surrounds the incision thereby providing access to the tissue surface opened by the incision beneath the base support unit. The kit also includes at least one securing mechanism removably attachable to the topside and proximate to the opening of the base support unit. In addition, the kit also includes at least one tissue hook and a corresponding retractable member, wherein each tissue hook has a tissue engagement portion and a mounting portion.

The tissue engagement portion of the tissue hook is capable of engaging at least a portion of the periphery of tissue opened by the incision. The retractable member is at least substantially inelastic in its central longitudinal axis and flexible in at least one axis deviating from said central longitudinal axis and is adapted to receive the tissue hook (either removably or fixedly) at its mounting portion. The retractable member is adapted to be removably or fixedly attachable to said securing mechanism such that when the retractable member is retractable away from the incision, the tissue engagement portion retracts tissue to which it is engaged.

In another embodiment of the kit, the base support unit, securing mechanism and at least one retractable member are grouped in a first part. In a second part, the kit may include at least one tissue hook adapted to attach to the retracting member.

It is to be also noted that the above description of the various exemplary embodiments of the present method only serves to aid in the better understanding of said method. As such, the present method is not be construed as being limited to the illustrated embodiments and its corresponding description, but, only as defined in the appended claims that follow.

What is claimed is:

1. A tissue retractor comprising:
   a flat base support unit having a topside and an underside and including on the topside at least one securing mechanism that is formed as a layer, and the underside is flexible to be conformable to an external surface and designed to be removably attached to the external surface proximate to an incision;
   at least one tissue hook having an assembly of a tissue engagement portion and a mounting portion, the mounting portion including a transversely elongated slot that has a length transverse to a longitudinal direction of the assembly, wherein the tissue engagement portion is capable of engaging at least a portion of the periphery of tissue opened by the incision; and a retractable member that is inelastic along its central longitudinal axis and flexible around at least one axis deviating from said central longitudinal axis, wherein at least a portion of the retractable member includes a strap-like fastener strip that has its width larger than its thickness throughout an entire length of the strip and has a first end and a second end, the fastener strip adapted to receive the mounting portion of the tissue hook by movably passing through the slot of the mounting portion, and wherein the first end of said fastener strip is attached to the base support unit, and the second end of the fastener strip is threaded through the slot of the mounting portion and loops back to the base support unit to form a looped-back portion that is retractable, while movably passing through the slot of the mounting portion, in a direction away from the mounting portion such that the tissue engagement portion retracts tissue to which it is engaged, wherein the looped-back portion has an underside having a face that faces the securing mechanism on the topside of the base support unit and that includes a securing mechanism formed as a layer that is designed to removably attach the looped-back portion to the securing mechanism on the topside in a retracted position of the looped-back portion.

2. The retractor of claim 1, wherein the mounting portion further includes a shock prevention element connecting the aperture to the tissue engagement portion.

3. The retractor of claim 1, wherein at least an end portion of the fastener strip that includes the first end of the fastener strip has an underside that is designed to removably attach the end portion to the securing mechanism of the topside of the base support unit.

4. The retractor of claim 3, wherein the securing mechanism of the topside of the base support unit includes a first layer of a hook and loop fastener that has a shape selected from the group consisting of a continuous strip, a discrete element and a combination thereof, wherein the underside of the end portion of the fastener strip that includes the first end of the fastener strip includes a second layer of the hook and loop fastener designed to removably attach to said first layer.

5. The retractor of claim 4, wherein the surface shape of the continuous strip and the discrete element is selected from a group consisting of rectangular shapes, triangular shapes, elliptical shapes and any combination thereof.

6. The retractor of claim 4, wherein an end portion of the fastener strip that includes the first end of the fastener strip has an upper side that includes an attaching mechanism and the securing mechanism of the looped back portion of the fastener strip and the attaching mechanism include mutually attaching layers of a hook and loop fastener.

7. The retractor of claim 1, wherein the securing mechanism of the topside of the base support unit includes any one of an adhesive and a layer of a hook and loop fastener.

8. The retractor of claim 1, wherein the securing mechanism on the topside of the base support unit includes an adhesive.

9. The retractor of claim 1, wherein the underside of the base support unit includes an adhesive that is adapted to be removably attached to said external surface.

10. The retractor of claim 9, wherein the adhesive is a medical grade adhesive.

11. The retractor of claim 10, wherein the medical grade adhesive is selected from the group consisting of acrylic adhesives, silicone-based adhesives, urethane adhesives, synthetic rubber adhesives and natural rubber adhesives.

12. The retractor of claim 9, wherein the base support unit is formed by an adhesion pad.

13. The retractor of claim 1, wherein the underside of the base support unit comprises at least one suction cup adapted to be removably attachable to said external surface.

14. The retractor of claim 1, wherein the base support unit is an incision drape.

15. The retractor of claim 14, wherein the incision drape is a medical grade plastic.

16. The retractor of claim 15, wherein the incision drape is adapted to be antimicrobial and to adhere to the wound edge, thereby providing a sterile surface.

17. A method of retracting tissue opened by an incision with a tissue retractor as recited in claim 1, said method comprising:

attaching the base support unit on the external surface proximate to the incision;

threading the fastener strip, that has its first end attached to the base support unit, through the slot of the mounting portion of the tissue hook to form the looped back portion of the fastener strip;

engaging the tissue hook engagement portion with at least the periphery of the incision;

retracting the looped-back portion through the slot of the mounting portion in a direction away from the incision such that the tissue engagement portion of the tissue hook retracts tissue it is engaged with to a desired distance; and securing the securing mechanism of the retracted looped-back portion to the securing mechanism on the topside of the base support unit to secure the looped-back portion in the retracted position.

18. The method of claim 17, wherein the attaching of the base support unit is at least such that the securing mechanism of the topside is at least substantially parallel to the direction of the incision.

19. The method of claim 17, wherein the securing mechanism of the topside includes a layer of a hook or loop fastener.

20. The method of claim 17, wherein the retractable member comprises a hook and loop fastener strip.

21. The retractor of claim 1, wherein an end portion of the fastener strip that includes the first end of the fastener strip has an upper side that includes an attaching mechanism and the securing mechanism of the looped back portion of the fastener strip and the attaching mechanism include mutually attaching layers of a hook and loop fastener.

22. The retractor of claim 1, wherein an end portion of the fastener strip that includes the first end of the fastener strip has an upper side that includes an attaching mechanism and the securing mechanism of the looped back portion of the fastener strip and the attaching mechanism of the end portion of the fastener strip include an adhesive.

23. The retractor of claim 1, wherein the retractable member is integrally formed with the base support unit.

24. A tissue retraction assembly, comprising:

a hook member formed with a distal tissue engagement feature configured to engage a periphery of an opening in a patient's body such that when the hook member is pulled away from the opening, the distal engagement feature remains in contact with the periphery of the opening to pull the periphery outward, the hook member also being formed with a proximal slot;

a longitudinally inelastic flexible strap extending through the proximal slot of the hook member to form a loop, the strap defining first and second end segments; and a flexible flat base defining a bottom surface having adhesive thereon for adhering to a portion of the patient without surrounding the opening in the patient's body, the flexible base conforming to the portion of the patient, the first end segment of the strap being engaged with the base, the second end segment of the strap being removably engageable by hand with a top flat surface of the base such that the second end segment can be detached from the base by hand, pulled to cinch the loop formed by the strap and thereby pull the hook member to retract tissue away from the opening in the patient's body, and reattached to the top surface of the base by simply pressing the second end segment onto the top flat surface of the base by hand to thereby hold the loop cinched.

25. The assembly of claim 24, wherein the distal tissue engagement feature includes three curved fingers.

* * * * *